United States Patent [19]

Hood

[11] Patent Number: 5,261,922
[45] Date of Patent: Nov. 16, 1993

[54] IMPROVED ULTRASONIC KNIFE

[76] Inventor: Larry L. Hood, 25652 Nottingham Ct., Laguna Hills, Calif. 92653

[21] Appl. No.: 839,411

[22] Filed: Feb. 20, 1992

[51] Int. Cl.⁵ ............................................. A61B 17/32
[52] U.S. Cl. .................................. 606/169; 606/169; 30/355
[58] Field of Search ............... 604/22; 128/24 AA; 606/169-171; 30/144, 346.56, 355

[56] References Cited

U.S. PATENT DOCUMENTS

| | | | |
|---|---|---|---|
| 2,845,072 | 7/1958 | Shafer | 604/22 |
| 3,086,288 | 4/1963 | Balamuth et al. | 178/24 AA |
| 3,654,701 | 4/1972 | Hastings, Sr. | 30/346.56 |
| 3,805,787 | 4/1974 | Banko | 604/22 |
| 3,888,004 | 6/1975 | Coleman | 128/24 AA |
| 3,898,992 | 8/1975 | Balamuth | 128/24 AA |
| 4,188,952 | 2/1980 | Loschilov et al. | 604/22 |
| 4,634,420 | 1/1987 | Spinosa et al. | 404/22 |
| 4,960,419 | 10/1990 | Rosenberg | 604/22 |
| 4,979,952 | 12/1990 | Kubota et al. | 604/22 |
| 4,988,334 | 1/1991 | Hornlein et al. | 604/22 |
| 5,026,387 | 6/1991 | Thomas | 606/169 |
| 5,047,043 | 9/1991 | Kubota et al. | 604/22 |

Primary Examiner—C. Fred Rosenbaum
Assistant Examiner—Michael Rafa
Attorney, Agent, or Firm—Knobbe, Martens, Olson & Bear

[57] ABSTRACT

Disclosed is an improved ultrasonic knife of the type for surgical incision in various types of tissue and/or for the removal of cement within the body. The knife has a reduced thermal footprint to minimize thermally induced tissue damage. Tooth configuration on the knife cooperates with the stroke of the ultrasonic drive to produce efficient cutting, as well as tactile feedback to the surgeon with respect to the rate of cutting, and changes in tissue density. Ultrasonic knife tip extenders are also disclosed for advancing the ultrasonic knife tip through the working channel of an endoscope. Methods utilizing the foregoing apparatus are also disclosed.

22 Claims, 8 Drawing Sheets

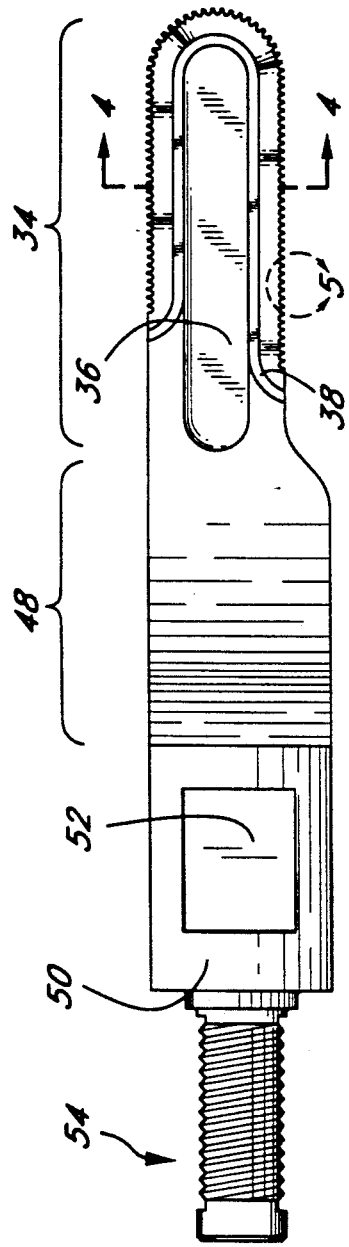
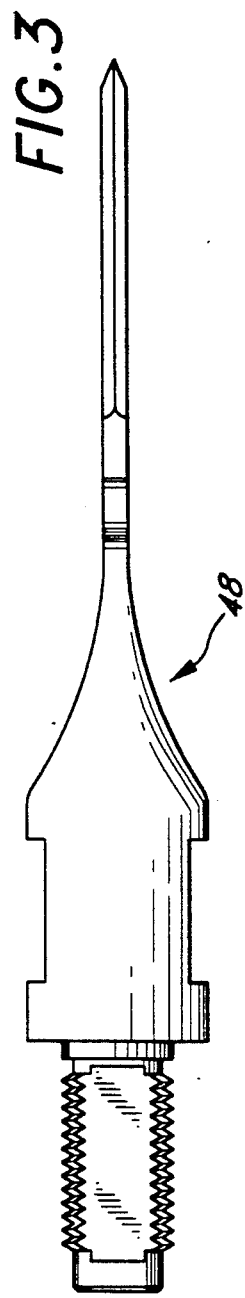
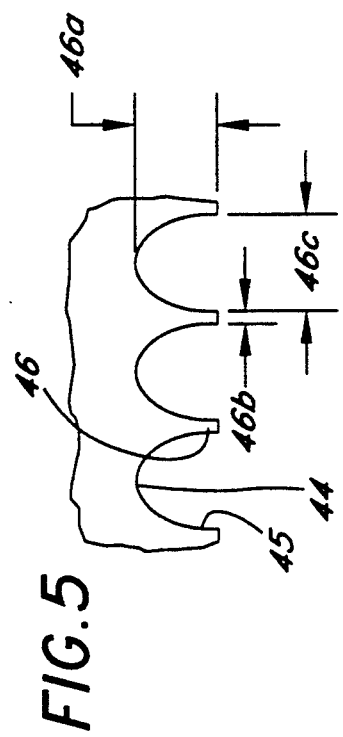
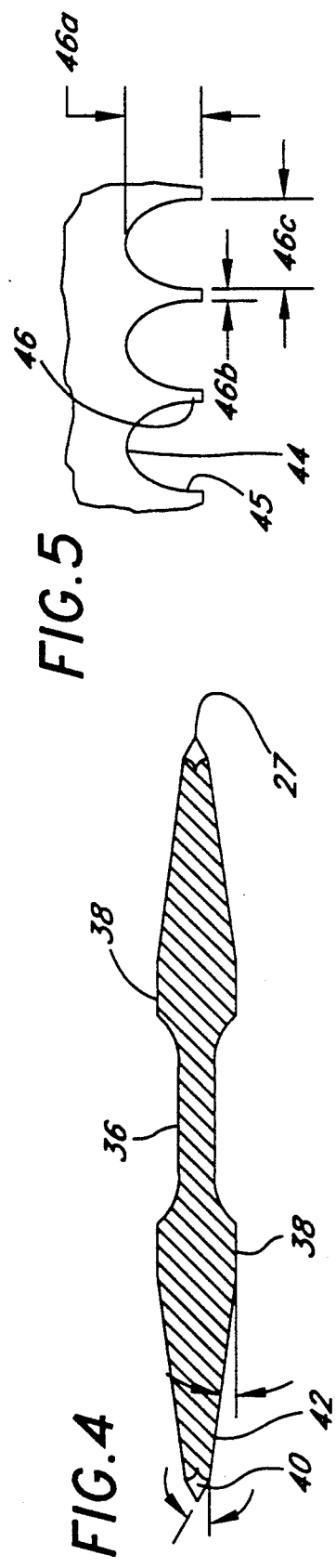
FIG.2
FIG.3
FIG.5
FIG.4

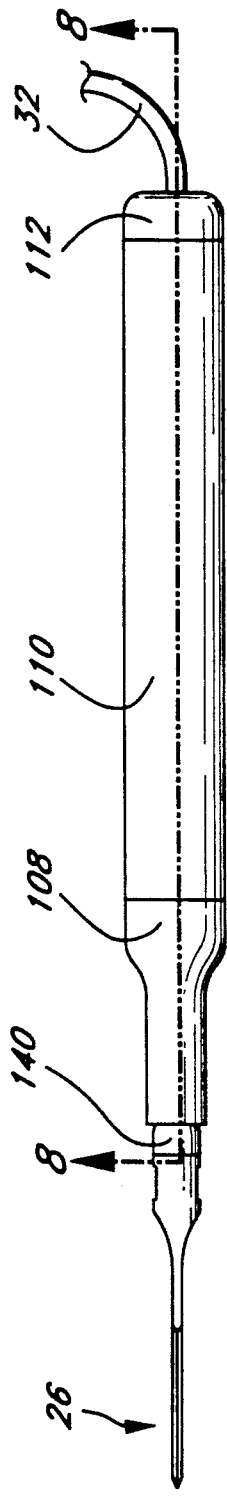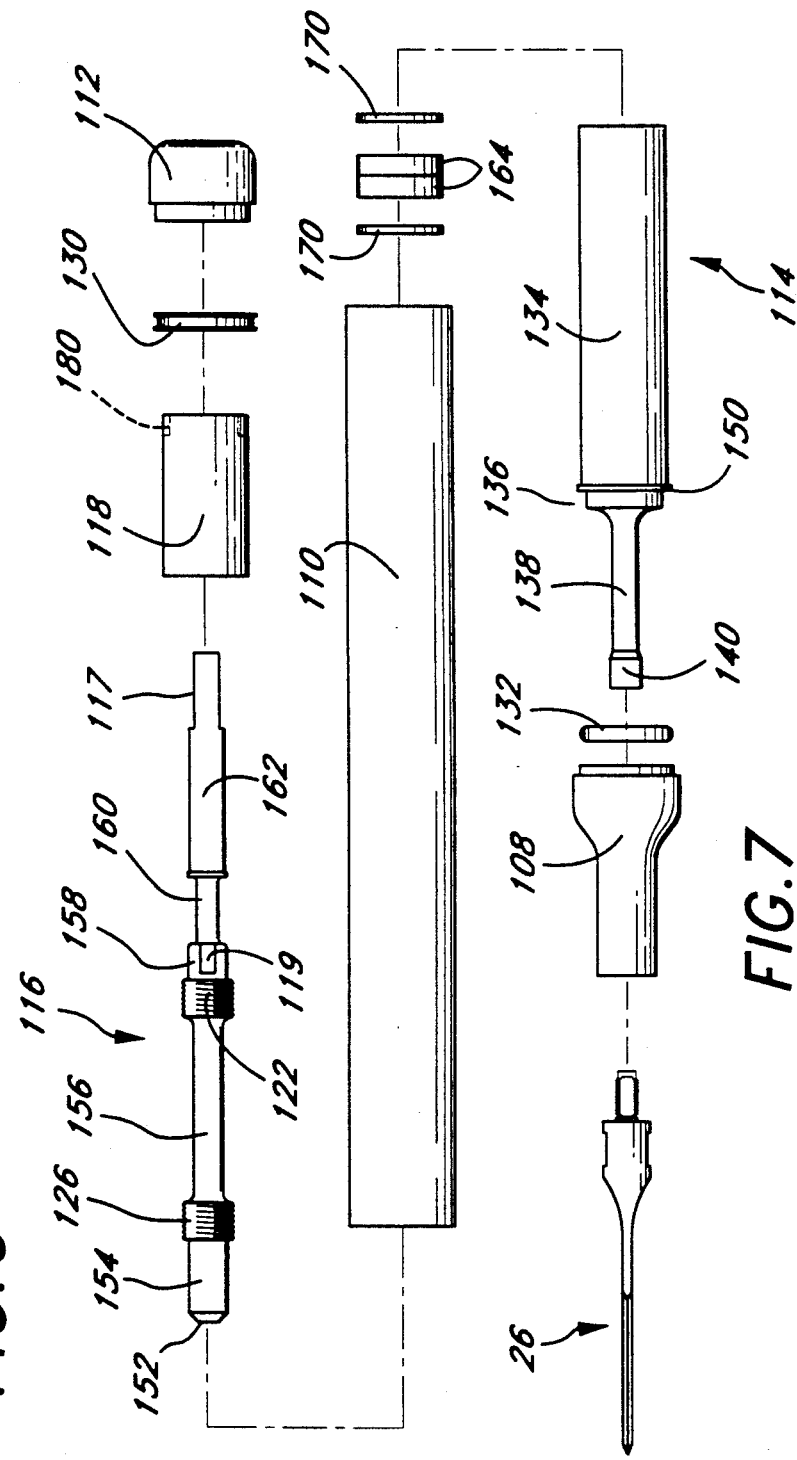
FIG. 6
FIG. 7

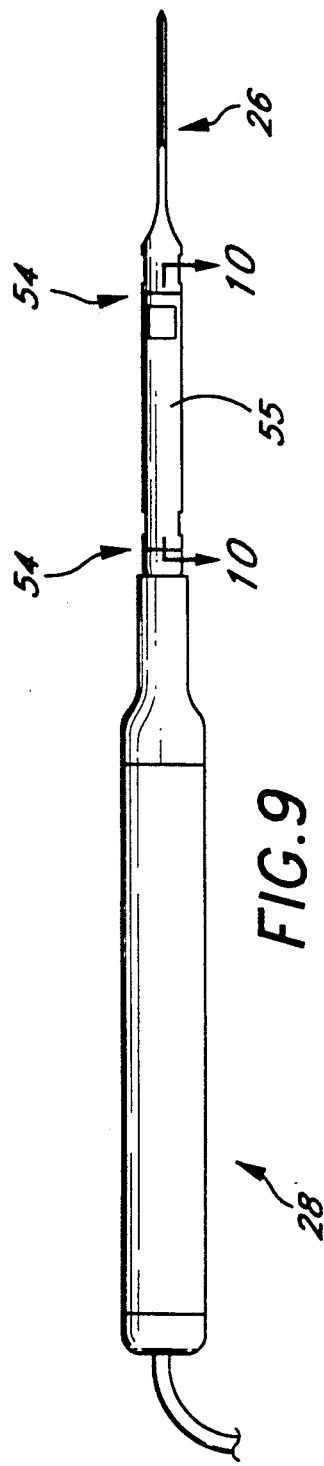
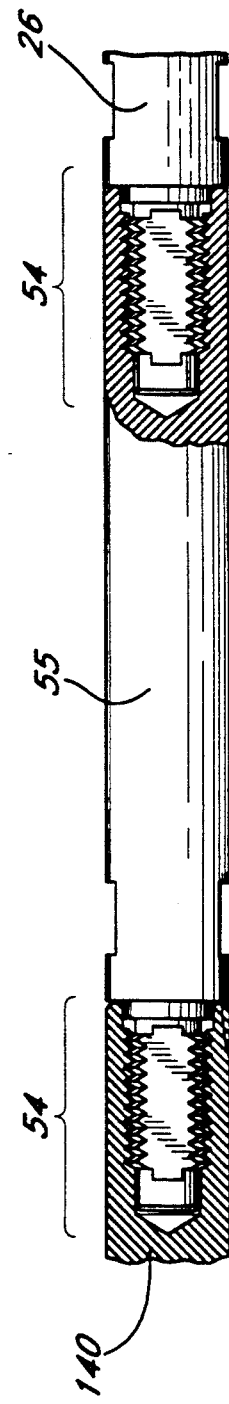
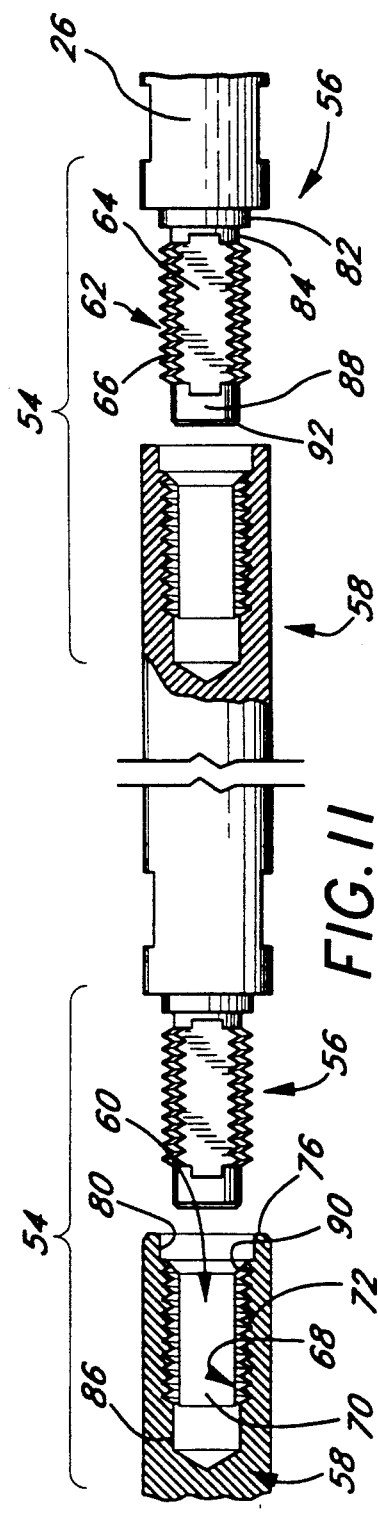

IMPROVED ULTRASONIC KNIFE

BACKGROUND OF THE INVENTION

1. Field of the Invention

The invention relates generally to ultrasonic surgical instruments and, more particularly, to an improved ultrasonic knife.

2. Description of Related Art

The use of ultrasonic surgical instruments for cutting various types of tissues and/or removal of cement within the body is well known. An ultrasonic surgical instrument commonly comprises a knife blade connected to an ultrasonic oscillation source. The edge of the knife blade is brought into direct contact with the tissue being operated on and vibrated at ultrasonic frequencies. Conventional ultrasonic surgical instruments are used to cut or shatter a variety of living tissues such as the soft tissue found in cataracts, the cartilaginous tissue found around bones, and the osseous tissue of the bone itself. Surgeons are also finding ultrasonics to be an excellent tool for the removal of cements, such as, for example, Polymethylmethacrylate (PMMA), which is frequently used to affix a prosthetic hip joint to the existing femur.

The mechanical oscillation at the end of an ultrasonically vibrated knife blade reduces the amount of pressure required to initiate and propagate a cut or incision which allows the surgeon to concentrate more on the direction of cut. Advantageously, the surrounding tissue experiences minimal stretching and tearing as compared to procedures utilizing conventional stationary blades.

Problems which can be associated with ultrasonic surgery include excessive heat generation, tearing of tissue, or inadvertent cutting of nearby structures. Other problems have been associated with the ergonomics of ultrasonic surgical instruments. Moreover, different surgeons desire different tactile feedback and operating performance. The prior art generally has demonstrated a lack of understanding of the tactile feedback necessary to carefully re-sect different types of living tissues with one particular knife.

Some examples of prior art have attempted to reduce the "thermal footprint" of the ultrasonic cutting tool. For example, in U.S. Pat. No. 5,026,387 issued to Thomas, an ultrasonic surgical cutting tool is disclosed which automatically shuts off upon removal from the tissue. The automatic shut-off switch reduces the time that the surgical cutting knife is vibrating and thus decreases its heat buildup. U.S. Pat. No. 4,188,952 issued to Loschilov et al., discloses an ultrasonic surgical instrument which relies on a pentagonal cross section to reduce the thermal damage to the side surfaces of the tissue being cut because of a smaller area of surface contact. The thermal footprint of an ultrasonic surgical knife is defined by its surface area in contact with the tissue, both frontally and on the sides. In general, the inventions of the prior art had been fairly simple in their approach to reducing thermal footprint of ultrasonic blades and have failed to provide any real sophistication for the design of these tools which is sorely needed.

A need exists for an improved ultrasonic surgical blade which gives better feedback when cutting through various types of tissue and provides enhanced ergonomics to surgeons.

SUMMARY OF THE INVENTION

There is provided in accordance with one aspect of the present invention, a method of cavitation-assisted surgery utilizing an ultrasonic knife. An ultrasonic knife is provided, of the type having a source of ultrasonic vibrations, a knife blade coupled to the source, and a control for selectively causing the source to produce ultrasonic vibrations in the knife blade.

The source is activated to induce reciprocal movement of the knife blade throughout a predetermined axial stroke amplitude, and the blade is contacted with the tissue to be cut. The formation of cavitation bubbles is induced in the fluid media surrounding the knife blade, and the cavitation bubbles are thereafter permitted to implode, thereby producing shockwaves for breaking the tissue bond adjacent the cutting edge of the knife blade.

Preferably, the inducing formation of cavitation bubbles step is accomplished by providing the knife blade with a surface texture for creating cavitation bubbles. In one embodiment, the surface texture comprises a plurality of rounded spherical or hemispherical irregularities, having a width within the range of from about 20 microns to about 100 microns. The surface irregularities may be either pitted recesses such as by acid etching or other techniques known in the art, or beads adhered to the surface of the blade.

The inducing formation of cavitation bubbles may alone or in addition to the blade texturing be enhanced by providing a plurality of surfaces on the cutting edge of the knife, which extend generally perpendicular to the longitudinal axis of ultrasonic energy propagation through the knife. In a further aspect of the present method, inducing formation of cavitation bubbles may also be enhanced by modulating the energy driving the knife to include at least a first low frequency component for increasing cavitation, and a high frequency component for minimizing the depth of penetration of heat generated by the blade into the adjacent tissue.

In accordance with a further aspect of the present invention, there is provided an ultrasonic knife for conducting wet, cavitation-assisted surgery, or dry, cauterizing surgical procedures. The knife comprises a source of ultrasonic vibrations, a knife blade coupled to the source, and a control for selectively causing the source to produce ultrasonic vibrations, thereby inducing reciprocal movement of the knife blade through a predetermined stroke.

The blade comprises at least two teeth defining a recess therebetween, wherein the distance between the two teeth is no more than about the predetermined stroke. Preferably, the distance between the two teeth is no more than about 80% of the predetermined stroke. The predetermined stroke is preferably within the range of from about 0.001 to about 0.002 inches, and, most preferably, the predetermined stroke is approximately 0.0015 inches.

The width of each of the teeth is within the range of from about 30% to about 60% of the stroke, and preferably the width of each of the teeth is about 50% of the stroke. Preferably, a plurality of teeth are provided on the blade, extending throughout the cutting surface thereof.

The recess formed between each two adjacent teeth comprises a bottom portion and two sidewall portions, each sidewall portion terminating in a tooth edge at the most lateral extent, and the distance between the bottom of the recess and the tooth edge is within the range of from about 20% to about 100% of the stroke. Preferably, the distance between the bottom of the recess and the tooth edge is about 80% of the stroke.

Preferably, the bottom of the recess and sidewalls of the recess merge to form a generally parabolic shape. Alternatively, the two sidewalls are generally parallel to each other, and generally perpendicular to the bottom of the recess. In general, the two sidewalls and the bottom of the recess define a continuous boundary of the recess, and at least a portion of the boundary extends perpendicular to the longitudinal axis of ultrasonic energy propagation through the knife, and at least a second portion extends generally parallel to the longitudinal axis of ultrasonic propagation energy through the knife.

In a preferred embodiment, in which the thermal footprint of the knife is minimized, the blade comprises a generally planar body portion having a proximal connection end and at least one cutting edge thereon, and a width in a central region thereof which is less than the width at at least one point between the central region thereof and the cutting edge.

In accordance with a further aspect of the present invention, there is provided a blade for ultrasonic surgery. The blade comprises a generally planar body having at least one cutting edge thereon, and, preferably, two cutting edges thereon having different surface texture or draft configurations. A coupler is provided for coupling the body onto a source of ultrasonic vibration, and a plurality of teeth are provided on each cutting edge, each adjacent pair of teeth forming sidewalls for a recess therebetween. The width of the recess is optimally no more than about 0.0015 inches. Preferably, at least one shallow recess is provided on the side of the planar body for reducing the thermal footprint of the blade.

Further advantages and features of the present invention will become apparent to one of skill in the art from the detailed description of preferred embodiment which follows, when taken together with the claims and drawings.

BRIEF DESCRIPTION OF THE DRAWINGS

FIG. 2 is a side view of the preferred cutting blade of the present invention;

FIG. 3 is a top view of the blade of FIG. 2;

FIG. 4 is a cross section of an edge of the blade of FIG. 2 along line 4—4;

FIG. 5 is an enlargement of the teeth of the blade of FIG. 2 illustrating the preferred depth and pitch;

FIG. 6 is a top view of the ultrasonic surgical tool of FIG. 1;

FIG. 7 is an exploded view of the ultrasonic surgical tool of FIG. 1;

FIG. 9 is a top view of an ultrasonic medical tool of the present invention showing a handpiece, an extender and a preferred blade.

FIG. 10 is a partial cross-sectional view of the ultrasonic medical tool of FIG. 9 taken along line 10—10 illustrating two junctions of the present invention;

FIG. 11 is an exploded partial cross-sectional view of the junctions of FIG. 10;

FIG. 12a is a cross-sectional view of the junction of FIG. 12 taken along line 12a—12a;

DETAILED DESCRIPTION OF THE PREFERRED EMBODIMENT

In accordance with the present invention, the improved ultrasonic surgical tool provides enhanced tactile feedback to the surgeon and may be adjusted to customize the feedback, depending on the preference of the surgeon. Additionally, the ultrasonic tool of the present invention can be configured to cut a wide variety of tissues by altering the blade structure alone, or in combination with the operating mode. The improved cutting tool is disclosed in the following specification with reference to the above-mentioned drawings.

Figure 1:
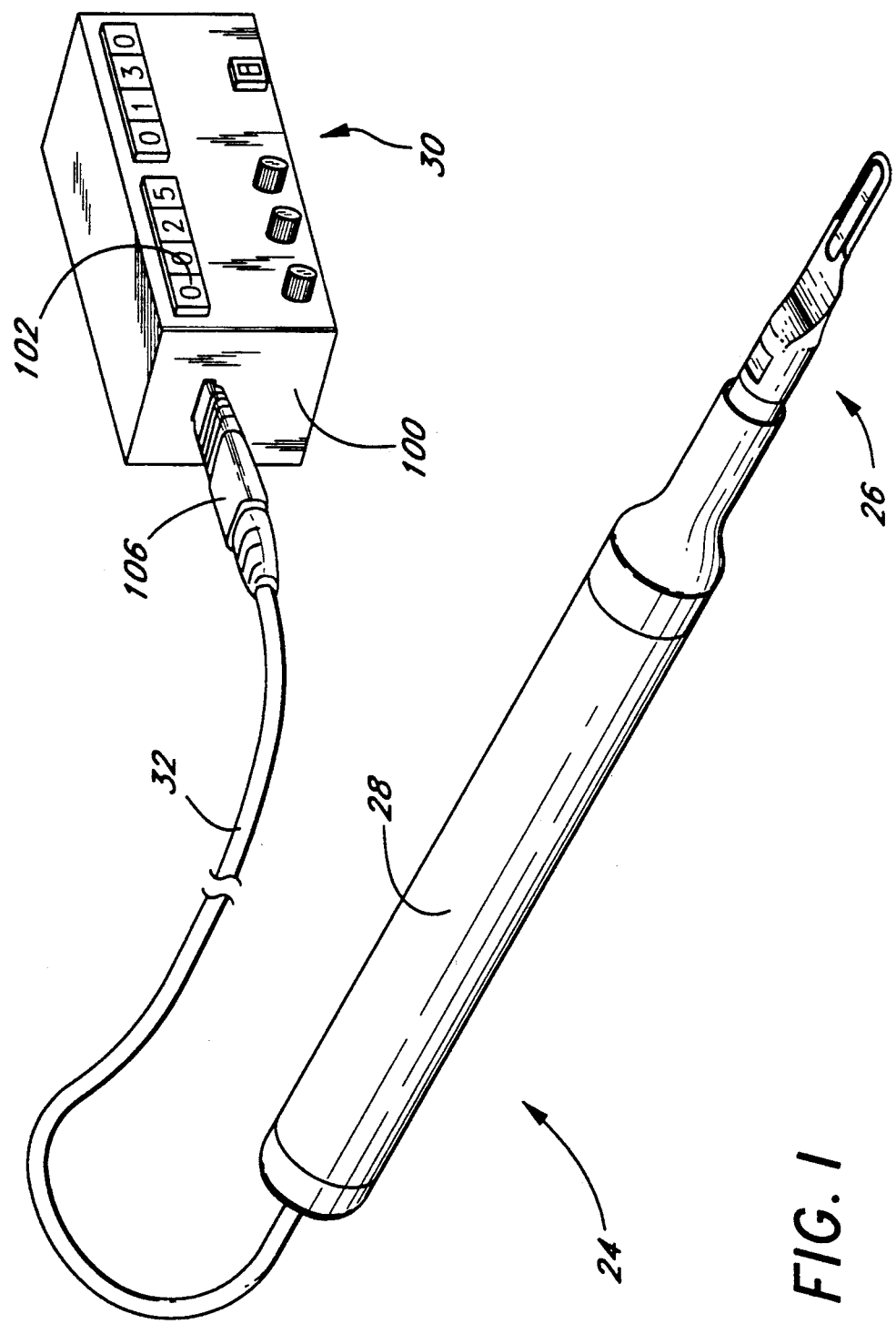
FIG. 1 is a schematic of the ultrasonic surgical tool system of the present invention.

As schematically shown in FIG. 1, an ultrasonic surgical system 24 ultimately vibrates a surgical blade 26. The blade 26 couples to an ultrasonic transducer (not shown) mounted in a handpiece 28 which is driven by a control system 30. A surgeon grasps the handpiece 28 and manipulates the blade 26 within a patient. A cable 32 transmits the ultrasonic driving signals from the control system 30 to the transducer within the handpiece 28.

Referring to FIG. 2, a preferred embodiment of surgical blade 26 is shown. The blade 26 includes a cutting section 34 at its distal end. As seen best in FIG. 4, the cross section of the cutting section 34 reveals a central channel or relief 36 machined into each side. The blade 26 is symmetric about a vertical plane through the center. The relief portion 36 allows the knife blade 26 to cut through various types of tissue with a minimum thermal footprint. The thermal footprint of a blade includes all the surfaces in contact with the tissue. At ultrasonic vibrations, the blade 26 can produce a substantial amount of heat from the frictional and ultrasonic contact with the tissue. The size of the relief 36, or percentage of area of the blade 26 out of contact with the tissue, directly affects the thermal footprint.

Adjacent the relief 36, tissue contact surfaces 38 extend for a distance generally parallel to the plane of the blade 26 towards the edge of the blade 26. In general, the width of each contact surface 38 in this plane is within the range of from about 0.0 to about 0.050 inches, and preferably within the range of from about 0.015 to about 0.025 inches.

These contact surfaces 38 represent the widest portion of the blade 26 along an axis transverse to the plane of the blade and produce a substantial amount of thermal friction with the tissue. Typically, the thickness of the blade through contact surface 38 is within the range of from about 0.010 to about 0.050 inches, and preferably within the range of from about 0.015 to about 0.025 inches. The size of the contact surfaces 38 also directly affects the thermal footprint. Smaller contact surfaces 38 reduce the thermal footprint of the blade 26.

The sharpened edge 27 of the blade 26 comprises a first taper 40 which is separated from the contact surface 38 by a second taper 42. Both the first and second tapers widen in the medial direction. The first taper 40 preferably ranges between about 10° and about 30°, and more preferably the first taper 40 is about 15°. The second taper 42 ranges between about 3° and about 45°, and more preferably the taper is about 8°. The angles of the tapered portions directly affect the character of cut and associated drag, or feel, experienced by the surgeon. A short taper, such as 45 degrees, would provide a duller blade generating more cavitation and drag. A longer, sharper taper would have substantially less tissue differentiation. The blade may have a continuous, sharp cutting edge as with conventional scalpels, or may have serrations or teeth as described below.

Referring now to FIG. 5, a preferred shape of serrations is shown enlarged. The serrations comprise parabolic-shaped recesses 44 separated by outwardly protruding teeth 46. The teeth 46 are spaced a certain distance apart to result in optimal cutting. Advantageously, the teeth 46 are separated by a distance 46c of less than one longitudinal stroke of the blade 26 to ensure that the tips of at least two teeth 46 cross any one point in a single stroke. The spacing 46c of the teeth 46 is most preferably eight-tenths of the blade stroke so that every tissue bond is contacted by two teeth 46 during each stroke, while internal material stresses are minimized.

The advantageous shape of the teeth 46 of the blade 26, shown in FIG. 5, provides an enhanced feel of cut at all times. A straight-edged ultrasonic knife blade will slip through tissue with a substantially constant resistance due to the blade edge being everywhere parallel to the tissue. Ultimately, the surgeon might apply more pressure than necessary, without realizing the depth of cut, and sever tissue not intended to be cut.

The contour of the recesses 44 on the ultrasonic blade 26 of the present invention changes the angle of the portion of the blade edge which strikes the tissue. During light cuts, the surgeon notices little resistance as bond severing occurs primarily at the tip edges of the teeth 46 parallel to the plane of uncut tissue ahead of the cutting edge. To provide ample light cutting surfaces, the width 46b of the tips of the teeth 46 are preferably 30–60% of the stroke amplitude, and most desirably the width 46b is 50% of the stroke.

Slightly more pressure results in cutting at the sidewalls 45 of the recesses 44, at least a portion of which is perpendicular to the plane of uncut tissue. The sidewalls 45 extend from the tip 46 of the teeth to the bottom 44 of the recess a sufficient distance to expose the perpendicular surfaces to the tissue. To ensure this exposure while retaining some strength for the extending teeth 46, the depth 46a or the sidewalls 45 is 20–100% of the blade stroke amplitude, and preferably the depth 46a is 80% of the stroke.

An increase in the downward force causes more of the sidewalls 45 perpendicular to the tissue, between the teeth 46 to contact the tissue, resulting in a change of resistance due to the increased surface area contact at a high vector angle. Thus, the surgeon experiences a greater resistance as the blade 26 is pressed harder into the tissue, and may adjust accordingly to prevent inadvertent injury to the patient.

The surface texture of the blade 26 directly affects the amount of frictional and ultrasonic heat generation, in addition to the level of cavitation. Highly polished surfaces tend to slide through the tissue with minimal friction and associated heat generation and sound transfer. The tapered surfaces 40, 42 and the recessed region 36 are preferably polished to minimize thermal damage to the tissue. Concurrently, if dry cutting is preferred, the contact surfaces 38 may be finished slightly rougher to ensure heat will build up mostly at this region and increased hemostasis will occur. Alternatively, the surfaces of the blade 26 may be roughened all over, a saline solution introduced at the operative site, and the blade oscillated at preferred rates to minimize thermal damage yet increase the amount of cavitation. Such a situation is seen in brain surgery where a constant stream of water, or other coolant fluid, is applied to the incision area, and the majority of the cut is cavitation-assisted.

Referring again to FIGS. 2 and 3, a transition section 48 alters the cross section of the blade 26 from the flat cutting section 34 to a generally cylindrical portion 50 comprising opposing wrench flats 52. The transition section 48 amplifies the gain of the ultrasonic oscillations. A coupling member 54 adjacent to the cylindrical portion 50 mates with an opposite sex coupling member on the distal end of the handpiece 28 or an extender. Due to the minimum time-constraints imposed by surgery, the coupling members are preferably rapid connect/disconnect types described below, with reference to FIGS. 9–16, showing an alternative embodiment with an extender 55.

FIGS. 9–11 illustrate two junctions on either end of the extender 55. FIG. 10 shows a partial cross section of the coupling between the handpiece 28 and the extender 55, and the extender 55 and the blade 26. Of course, it is understood that the coupling between the extender 55 and the preferred surgical blade 26 applies equally as well to a direct coupling between the blade 26 and the handpiece 28.

Each junction comprises a generally cylindrical male component 56 and a tubular female component 58 comprising a generally cylindrical recess 60 adapted to receive the male component 56. These components quickly connect by inserting the male component 56 into the female component 58 and rotating one component with respect to the other component, preferably through a relatively short rotational arc, and optimally about 90°, plus or minus 10°.

Only one junction will be referred to, as the junctions are identical. When joined, the junction produces a relatively high axial compression force, which is preferably uniformly distributed symmetrically about the contact surfaces between the two components to optimize the transfer of ultrasonic energy across the junction. Non-uniform distribution of the axial compression force about the longitudinal axis of the junction tends to decrease the efficiency of the transfer of energy across the junction, and can cause unwanted transverse motion (whipping) and may lead to premature mechanical failure.

Although FIGS. 9 through 14 illustrate the male component 56 extending in a distal direction, it is understood that the relationship of the male and female components can be reversed.

Figure 12:
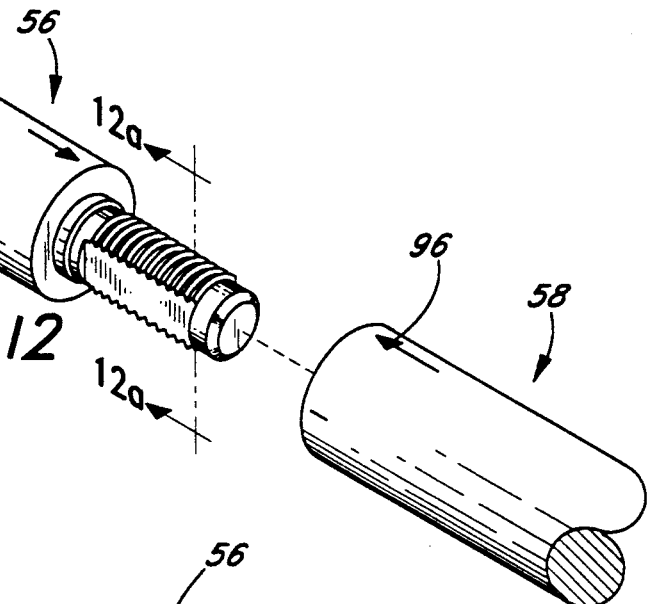
FIG. 12 is an exploded perspective view of one of the junctions of FIG. 10, illustrating the generally cylindrical male component on the proximal end of a surgical tool having a pair of splines interrupted by a pair of flats.
Figure 12A:
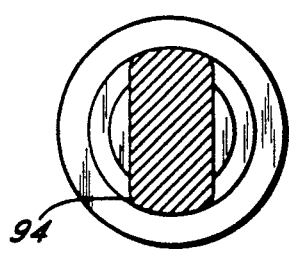

Referring to FIGS. 9-12, the male component 56 comprises at least two axially extending splines 62 spaced apart by at least two axially extending flats 64. Preferably, the male component 56 comprises two diametrically opposed splines 62 and two diametrically opposed flats 64, alternatively positioned around the circumference of the component, as seen in FIG. 12.

Each spline 62 comprises a plurality of external threads 66 preferably configured in accordance with the American National Standard for Unified Threads ("UN"). It will be understood that other thread configurations, such as the American National Standard Acme Screw Threads ("Acme"), can be used as well. It has been found preferable, however, to employ the UN thread design instead of others, such as the Acme thread design, primarily for manufacturing ease.

Advantageously, the thread pitch and the pitch diameter of the threads 66 and the length of the splines 62 are selected to produce high axial compression between the components without structural failure. It is also preferable to select a generally standard thread for manufacturing convenience. Additionally, the threads 66 must engage to produce high axial compression with little rotation. Preferably, circumferentially, 75% of the threads 66 engage with rotation of no more than about 90° plus or minus 10°. For example, in one preferred embodiment the splines 62 comprise a series of 4-56 UNS-2A threads 66 along a length of 0.215 inches, and in another embodiment, the splines 62 comprises a series of 5-48 UNF-2A threads 66 along a length of 0.250 inches In general, the spline 62 preferably comprises about twelve interrupted threads 66.

In general, the junction has a minimum of 45° of total engagement between the spline threads 66 to produce the high axial compression without mechanical failure. Preferably, the junction has an engagement between about 90° to about 179°, and most preferably about 173°(48% of 360°=172.8°). Thus, in a most preferred embodiment, the sum of the lengths of the threads 66 on the male component 56 measured in a circumferential direction preferably range from 90° to 179°, and more preferably equal 173°.

The circumferential length of each spline thread 66 (i.e., the circumferential width of each spline) depends upon the number of splines 62 employed. For example, in a most preferred embodiment having two splines 62, the length of the thread 66 in a single spline along the circumferential direction ranges between 45° and 89.5°, and preferably equals 86.5°.

Figure 15:
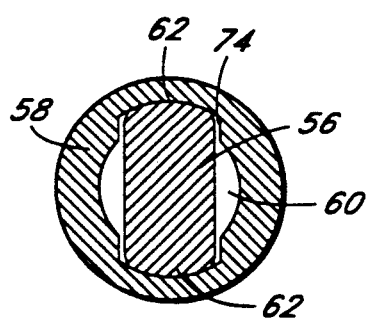
FIG. 15 is a cross-sectional view of the junction of FIG. 13 taken along lines 15—15.
Figure 16:
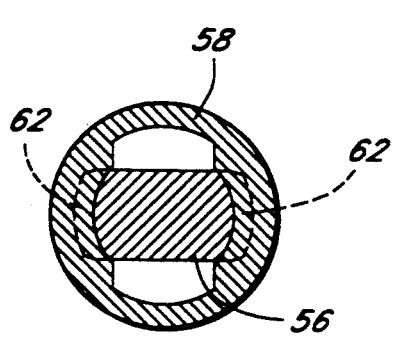
FIG. 16 is a cross-sectional view of the junction of FIG. 14 taken along lines 16—16.

The female component 58 likewise comprises at least two axially extending splines 68 and at least two axially extending flats 70, disposed on the recess 60 circumference in a corresponding relationship with the flats 64 and splines 62 on the male component 56, as best seen in FIGS. 9, 15 and 16. Preferably, the female component 58 comprises two diametrically opposed splines 68 and two diametrically opposed flats 70 alternatively positioned around the circumference of the recess 60, as best seen in FIG. 15. Each spline 68 comprises a plurality of internal threads 72 configured to match and engage with the threads 66 on the male component 56.

As discussed above, the sum of the length of the threads 72 around the circumference of the recess 60 is preferably not less than about 90° and not greater than about 179°, and most preferably equal 173°. Each spline thread length depends upon the number of splines 68 employed. For example, in a most preferred embodiment having two splines 68, the threads 72 of each spline extend around the circumference of the recess 60 for at least approximately 45° but less than approximately 89.5°, and preferably equal 86.5°.

The two splines 68 and two flats 70 alternately disposed on the interior circumference of the female component 58 recess 60 provide an axial key-way 74 for receiving the two opposing splines 62 on the male component 56, as shown in FIG. 15. The male component 56 is inserted into the recess 60 of the female component 58 and rotated to interlock the corresponding splines 62, 68 on the male and female components, as shown in FIG. 16. It is desired that minimum rotation of one component with resect to the other component will produce a junction which achieves a relatively high efficiency of energy transmission therethrough.

In general, it has been found that a high compression across the junction symmetrically distributed about its longitudinal axis optimizes energy propagation. Preferably, the thread design of the junction produces greater than about 100 pounds of axial compression force between the components with rotation of about 90°±10%. More preferably, a compression in excess of about 200 pounds will be achieved. As a result of higher compression, the ultrasonic pressure wave propagates across the junction with minimal energy loss.

It is preferred that the points of contact between the two joined surgical components be symmetric about the longitudinal axis of the male component 56 to uniformly distribute the compression force about the junction in the radial direction. As a result, the ultrasonic oscillation maintains its propagation along the longitudinal axis of the joined surgical components without deflection from that axis. If deflection occurs, the tool will tend to whip resulting in undesired heat build-up and loss of energy at the tool tip.

In this regard, the female component 58 preferably additionally comprises an annular engagement surface 76 on the proximal end thereof which contacts a corresponding annular engagement surface 78 of the male component 56. Preferably, the engagement surface 76 of the female component 58 extends radially outwardly along a plane substantially perpendicular the axis of the internal recess 60, and the engagement surface 78 of the male component 56 extends radially outward along a plane substantially perpendicular to the axis of the male component 56. Referring to FIG. 10, as the splines 62, 68, interlock, the two components draw together to force the engagement surfaces 76, 78, against each other, resulting in an axial compression force across the junction.

Preferably, the engagement surfaces 76, 78, are smoothly polished to produce a substantially liquid-tight seal between the components as the surfaces abut. In addition to optimizing energy propagation, a liquid-tight seal reduces cavitation erosion of the components at the junction and thereby extends the life of each component.

In a preferred embodiment, the female component 58 additionally comprises an axially extending, generally cylindrical counterbore 80 at the distal end of the recess 60 for receiving a generally cylindrical shank barrel 82 on the proximal end of the male component 56. The counterbore 80 and the shank barrel 82 are preferably centered with respect to the longitudinal axis of the male component 56. Preferably, the shank barrel 82 smoothly fits into the counterbore 80 to center the female component 58 with respect to the male component 56.

Advantageously, the male component 56 further comprises an undercut region 84 positioned between the engagement surface 78 and the spline so that the spline threads 66 are fully formed (i.e., no run-out region). As a result, the splines 62, 68 can be reduced in overall length, as will be understood in the art.

Referring to FIG. 11, the female component 58 preferably additionally includes a generally cylindrical pilot recess 86 for receiving a corresponding generally cylindrical tip barrel 88 at the proximal end of the male component 56. Preferably, the diameters of the pilot recess 86 and the tip barrel 88 substantially coincide with the minor diameter of the threads 72. Advantageously, the pilot recess 86 and the tip barrel 88 are centered about the longitudinal axis of the male component 56 for optimizing the concentricity of the engagement surfaces, between the components to optimize the longitudinal transfer of ultrasonic energy through the junction.

To facilitate rapid interconnection between the components, the female component 58 preferably additionally comprises an annular internal chamfer 90 and the male component 56 additionally comprises an annular tip chamfer 92. When the male component 56 is inserted into the female component 58, the chamfers 90, 92 ease the insertion by funneling the components together. Additionally, the edges of the leading spline threads 66 of the male component 56 preferably include a chamfer 94 to ease the engagement between the splines 62, 68 of the male component 56 and female component 58.

Figure 13:
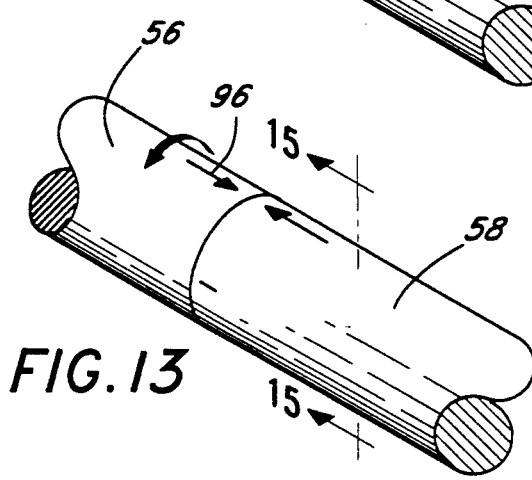
FIG. 13 is an assembly perspective view of the junction of FIG. 12 with a male component inserted into a female component.
Figure 14:
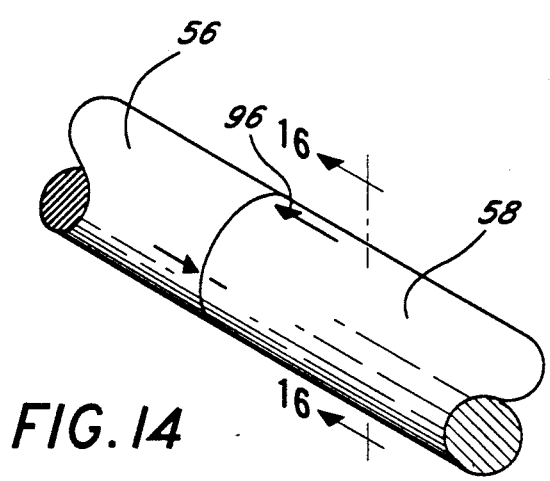
FIG. 14 is an assembly perspective view of the junction of FIG. 13 with the components rotated to engage corresponding splines of each component.

Referring to FIGS. 13-16, it is preferred that the surgical components include alignment arrows 96 etched on the exterior surface of the components to aid in the connection process. By aligning the arrows 96, the splines 62 of the male component 56 align with the key-way 74 of the female component 58, as seen in FIGS. 13 and 15. By rotating the components as shown in FIG. 14, the splines 62, 68 of the two components interlock, as shown in FIG. 16. Flat opposing surfaces 98 are provided on the exterior of all parts to receive a wrench to facilitate tightening and untightening of the junctions.

Those skilled in the art can manufacture the disclosed junction by processes known in the art. For example, the generally cylindrical male component 56 and the shank barrel 82 thereto can be cut into an end of the shank of a surgical component, such as the extender or the tool bit. The threads 66 can either be cold rolled onto the cylinder or preferably machine cut into the cylinder. The flats 64 can then be milled onto the component thereby interrupting the threads 66. Finally, the tip barrel 88 can be cut onto the distal end of the male component 56 such as by lathing operations well known in the art and the chamfers 92, 94, similarly added thereto.

The recess 60 of the female component 58 can be made by drilling the pilot hole recess 86 into the end of a surgical component. The counterbore 80 then can be milled and a portion of the pilot hole 86 tapped with the appropriate internal threads 72 by processes known in the art. The flats 70 can be milled and broached into the recess 60 thereby interrupting the threads 72 on the recess wall. Finally, the internal annular chamfer 90 can be drilled or milled to form a smooth transition from the counterbore 80 to the threaded recess 60.

Referring again to the improved ultrasonic surgical knife system 24 of FIG. 1, the control system 30 comprises an ultrasonic signal generator 100 which supplies an electric impulse to the handpiece 28, the voltage of which can be varied at different frequencies and with different wave-shapes. The signal may, for example, be a pure sinusoidal wave or may be modulated with one or more other frequencies. Alternatively, the signal may be a stepped or spiked pulse. In a preferred embodiment, the ultrasonic generator 100 transmits a signal of between 20–80 kHz. More preferably, the signal is at about 60 kHz. The signal generator 100 includes a liquid crystal or other display device 102 for convenient display of selected power or frequency mode. The signal generator 100 may, for example, transmit a constant amplitude signal at a constant frequency, or alternate one or both of these parameters. The cutting power level is normally selected as a percentage of maximum cutting power. Although not illustrated in FIG. 1, an audio output indicative of mode changes and present mode is preferably included which is responsive to the ultrasonic signal generator output 100.

The signal transmits through a multi-conductor shielded cable 32, for safety and durability, to the handpiece 28 which imparts ultrasonic, generally longitudinal, movement to the surgical blade 26. As will be described more fully later, high-efficiency piezo-ceramic washers 164 which generate the ultrasonic vibrations within the handpiece (FIG. 7), allow a thin high-flex cable 32 to be used. The electronic signals are a lower than usual voltage not requiring a thick cable, which gives the surgeon added freedom to maneuver the handpiece 28. A high quality auto-clavable connector 106 couples the cable 32 to the signal generator 100.

Referring to FIGS. 6 and 7, the outer protective cover of the handpiece 28 generally comprises a nose cone 108, a cylindrical casing 110 and an end cap 112 of durable stainless steel or other corrosion resistant material. Advantageously, the protective cover is stainless steel and the sections are sealed hermetically, to protect the internal components from the corrosive fluids of surgery and temperatures in a steam autoclave. The handpiece 28 is preferably about 6 inches long and ½ inch in diameter.

The distal end of the handpiece 28 is the end proximate the blade 26, and the proximal end is the end proximate the cable 32. An acoustic horn 114 transmits standing pressure waves from the piezo-ceramic washers 164 to the blade 26. A central bolt 116 extends substantially the length of the handpiece 28 and provides a central coupling member rigidly joining the internal elements, as seen in cross section in FIG. 8. A heel slug 118 includes internal threads 120 for engagement with external threads 122 of the central bolt 116. The horn 114 also includes internal threads 124 which couple with external threads 126 on the central bolt 116. The piezo-ceramic washers 164 include a central bore 128 sized to fit over the external threads 122 of the central bolt 116. The horn 114 and heel slug 118 compress the washers 164 therebetween via longitudinal movement along the central bolt threads 122, 126. The piezo-ceramic washers 164, in combination with portions of both the horn 114 and heel slug 118, comprise an electromechanical transducer, converting electrical energy to mechanical pressure waves.

A rear annular bulkhead 130 is silver soldered to the rear of the central bolt 116 and supports the outer casing 110 at the proximal end of the handpiece 28. The interface between the outer circumference of the bulkhead 130 and cylindrical casing 110 provides a hermetic seal and a solid ground connection. Additionally, an O-ring 132 disposed between a front flange of the horn 114 and the nose cone 108 provides a fluid-tight interface. The piezo-ceramic washers 164, and all other internal components shown in FIG. 8 between the seals 130, 132, are thus enclosed within the cylindrical casing in a fluid-tight manner allowing the handpiece 28 to be immersed in a steam autoclave without harm.

The horn 114 comprises generally three sections, a cross-sectionally enlarged section 134, a transition section 136 and a narrow section 138 (see FIG. 7). The narrow section 138 at the distal portion of the horn 114 includes a female junction component 140 adapted to receive a male junction component (not shown) of a surgical blade 26, or other surgical component. The mechanical energy which is produced by the piezo-ceramic washers 164 propagates along the horn 114 and amplifies at the transition section 136.

As is well known in the art, decreasing the cross section of a structure transmitting longitudinal pressure waves increases the stroke, i.e., produces a positive gain in longitudinal oscillation. A stepped horn produces a gain which is approximately equivalent to the ratio of the larger area to the smaller area of the horn 114, while a more gradual change in diameter produces a gain equivalent only to the ratio of the diameters. Moreover, the location of the cross-sectional changes along the structure affects the degree of gain produced, as described below.

Thus, by adjusting the change in cross section of the horn 114, the shape of the dimensional transition, and the location of the dimensional transition, a specific gain may be obtained to tailor the stroke of the blade 26 for optimum performance. Preferably the gain achieved by the transition section 136 works in conjunction with a transition section of the blade 26 to produce an optimum longitudinal amplitude at the blade tip. The longitudinal amplitude of the blade 26 is preferably between 0.00025 and 0.004 inches peak-to-peak, and more preferably 0.0015 inches peak-to-peak, reducing the chance of material failure and controlling the energy for a fixed thermal footprint.

The piezo-ceramic washers 164 remain in a stationary, compressed state between the horn 114 and the heel slug 118 and thus occupies a node of a standing wave created along the heel slug-washer-horn combination. At the nodes of vibration there is no motion but maximum stress. Nodes are spaced exactly one half wavelength apart and thus from the piezo-ceramic washers 164, nodes occur every half wavelength down the horn 114 (e.g. front transition 136).

Anti-nodes are points of absolute maximum amplitude, experience the largest longitudinal movement and the least stress, and are located ¼ wavelength from each node. The closer the location of the cross-sectional change 136 to a node of vibration, the greater the gain realized, because the ultrasonic energy is stored as internal potential at these points, as opposed to kinetic energy at the anti-nodes.

The elongated, cylindrical horn 114 preferably includes one step concentrator to tailor the gain to cause a preferred blade 26 to function optimally; i.e., to preferably stroke from 0.00025 to 0.004 inches, peak-to-peak, and more preferably at 0.0015 inches, peak-to-peak. The small stroke advantageously reduces internal stresses in the horn 114 and blade 26 and thus reduces the chance of material failure.

The proximal end of the horn 114 defines an aperture leading to a central cylindrical cavity 142 sized to receive the distal end of the central bolt 116. The cavity 142 includes internal threads 124 which mate with external threads 126 on the central bolt 116. The cavity 142 extends axially in the distal direction, past the internal threads 124, and ends at a chamfered portion 144. The central bolt 116 includes opposing axial flats 119 for a wrench-assisted insertion into the cavity 142. A second set of flats 117 allows a wrench-assisted connection of the heel slug 118 over the bolt 116.

The majority of the enlarged section 134 comprises a solid cylinder to optimize ultrasonic energy propagation. The horn 114 is thus preferably constructed of a high strength material which efficiently propagates ultrasonic energy. More preferably, the horn 114 is constructed of titanium.

The distal portion of the horn 114 includes a female coupling portion 140, as described above. The distal portion of the horn 114 additionally comprises a central lumen 146 extending proximally from the female coupling 140 preferably throughout the length of the narrow section 138. The lumen 146 extends slightly past the transition section 136. The lumen 146 assists in amplifying the ultrasonic energy propagated down the horn 114. As described previously, pressure waves crossing a reduction in the cross-sectional area of a structure experience a gain. The lumen 146 defines a tubular section at the distal portion of the horn 114, further reducing the cross-sectional area of the material of the narrow section 138.

The overall length of the horn 114 is preferably less than about 2.5 inches, and more preferably the length of the horn 114 is 2.40 inches. The horn 114 is sized so that the front coupling junction 140 experiences a minimum of stress from being positioned close to an anti-node of vibration. The transition section 136 is desirably less than 0.75 of an inches from the farthest front portion of the horn 114, and more desirably the transition section is 0.600 inches from the front of the horn 114. The enlarged section 134 has a diameter of no more than ½ inch to fit comfortably in the hand of a surgeon, and more preferably the diameter of the enlarged section is 0.425 inch. Advantageously, the inside diameter of lumen 146 in the narrow section 138 of the horn 114 is less than about 0.1 inches to provide a sufficient wall thickness of the frontal section to minimize stress failure. More preferably, the diameter of the lumen 146 is about 0.07 inches. The outer diameter of the narrow section 138 of the horn 114 is preferably no more than about 0.25 inches, and more preferably the outer diameter of the narrow section is 0.125 inches. Advantageously, an exterior annular flange 150 at a position proximal to the transition section 136 provides a shoulder against which the O-ring 132 abuts. The nose cone 108 of the outer cover compresses the O-ring 132 rearward against the flange 150 in a semi-rigid manner, and in a fluid tight manner between the inside diameter of the tubing 110 and the outside diameter of the horn 114.

Figure 8:
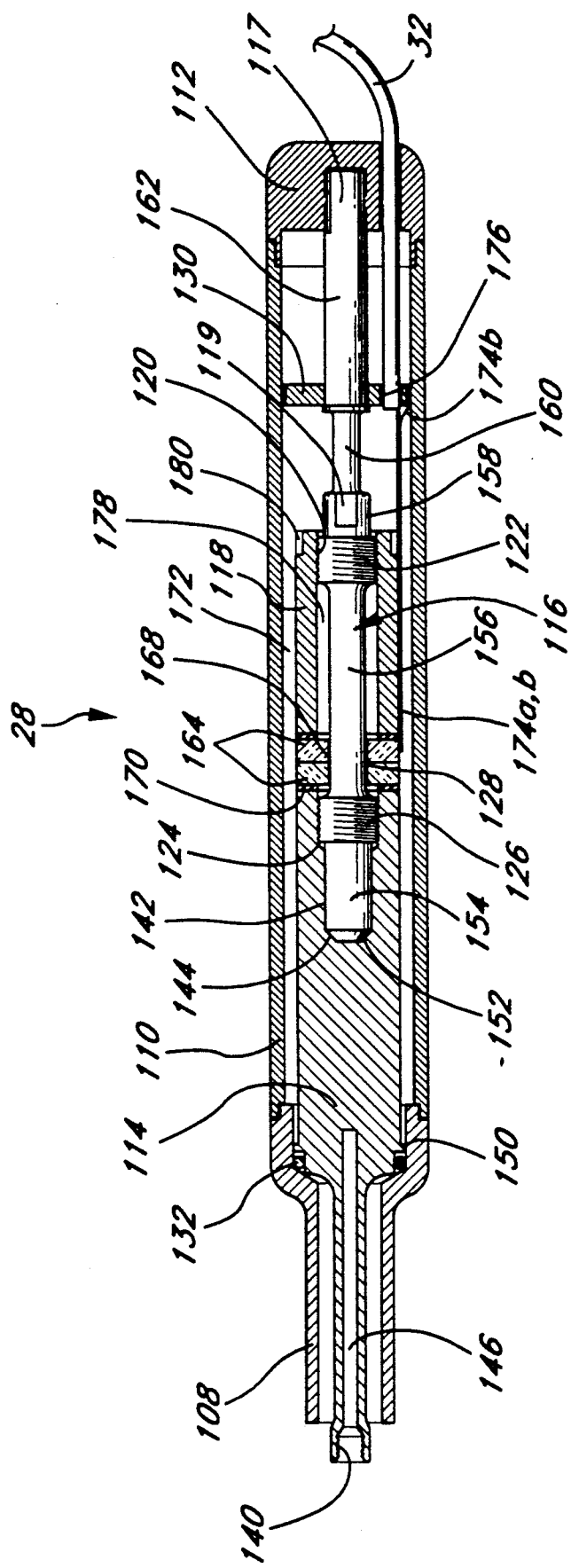
FIG. 8 is a cross section of the ultrasonic surgical tool along lines 8—8 of FIG. 6.

Referring to the cross-sectional view of FIG. 8, the length of the central bolt 116 is shown. The central bolt 116 comprises a solid, generally cylindrical metallic rod with a chamfer 152 at the distal end of a distal cylindrical portion 154. The distal cylinder 154 fits in the distal cavity 142 of the horn 114, as previously described. The distal chamfer 152 bottoms out at the internal chamfer 144, providing a flush stop for the central bolt-horn interface, thus more efficiently transmitting ultrasonic energy.

The distal thread region 126 separates the cylindrical portion 154 from a middle cylindrical region 156. The threads 126 are preferably 0.2 inches from the front of the central bolt 116, and the proximal section of threads 122 is located 1.4 inches further rearward. Preferably, the threads 126 are 10-56 UNS-2A type threads and configure to meet with similar internal threads 124 of the horn 114.

The middle cylindrical portion 156 extends through the central bore 128 of the piezo-ceramic washers 164. The washers 164 slide along the middle portion 156 to abut the horn 114 adjacent the distal threads 126 of the central bolt 116. The distal axial face of the washers 164 and proximal axial face of the horn 114 lie flush against a thin annular spacer 170 therebetween to optimize transmission of ultrasonic vibrational energy.

The proximal thread region 122 separates the middle region 156 from a cylindrical heel slug receiving portion 158. The bolt 116 terminates in a reduced diameter isolation region 160 and a rear bulk head support shaft 162. The rear thread 122 region is adapted to receive the heel slug 118. As stated previously, the heel slug 118 threads onto the central bolt 116, compressing the piezo-ceramic washers 164 against the horn 114. The rear-most portion of the heel slug 118 terminates at the transition of the central bolt 116 to the isolation region 160. The large change in diameter between the heel slug 118 and the isolation region 160 causes the isolation region to tend to vibrate at its own frequency, interfering with sound propagation at the fundamental frequency in this direction. In this manner, little ultrasonic energy is propagated rearward. The additional ¼ wave length 162 of the central bolt 116 forces the bulkhead to be an artificial node (a node and an anti-node separated by less than λ/4). This reinforces the stability of the bulkhead 130 location and minimizes any loading of the handpiece when the bulk head 130 is silver soldered to the Central bolt 116 and the inside diameter of the tube 110.

The material of the thin annular washers 164 is a piezo-ceramic compound of lead-titanate or lead-zirconate. Advantageously, two to eight washers 164 may be utilized, depending on the strength of vibration desired, and preferably there are two washers 164. These washers 164 include central bores 128 to fit over the middle cylindrical region 156 of the central bolt 116. The central bore 128 passes over the rear threads 122, and thus polymide tape 168 is wrapped around the central region 156 to fill the annular Void formed and hold the washers centered on the bolt 116.

Two very thin annular spacers 170 separate the piezo-ceramic washers 164 from the horn 114 and heel slug 118, and distribute the compressive forces evenly. A layer of electrically insulating material 166 covers the washers 164 and isolates them from the outer casing 110 of the handpiece 28. An air gap 172 between the insulating layer 166 and the casing 110 effectively isolates the ultrasonic vibrations from the outer casing. Preferably, the air gap 172 is approximately 0.17 inches, which has been found to reduce the radiation of internal heat to the outer casing 110. A "hot" electrode 174a and a ground electrode 174b connect to the appropriate piezo-ceramic washer 164 to effectuate mechanical vibrations. The electrodes 174 extend proximally from the piezo-ceramic washers 164 within the air gap 172. The "hot" electrode 174a passes through a small passage 176 in the bulkhead 130 and from there to the rear end cap 112 and a "hot" circuit of the connector 106 of the cable 32. The ground electrode 174b connects directly to the bulkhead 130 which is in electrical contact with the ground circuit of the connector 106.

As is well known in the art, piezo-ceramic materials produce mechanical vibrations upon excitation by an applied voltage. This mechanical vibration is caused by changes in the internal structure when under the influence of the external voltage. The layers of piezo-ceramic washers 164 are held under compression between the horn 114 and the heel slug 118. Preferably, the compression of the piezo-ceramic washers 164 is between 500 and 5000 psi, and most preferably about 1500 psi.

Aligning the washers so that the positive side of one abuts the positive side of another causes the washers to oppose each other's motion, and in effect double their amplitude vibrations. Such piezo-ceramic washers 164 held in compression are restricted from thickening; their internal stresses are transmitted to the surrounding compressive members in the form of pressure waves. The preferred piezo-ceramic configuration is a "Langewin sandwich" design.

As the waves propagate along the horn 114 and heel slug 118, the potential strain energy converts to kinetic energy and back, due to the wave-like nature of the signal. The heel slug 118 and adjacent isolation region of the central bolt 116 tend to quell the vibratory motion while the excellent energy transmittal properties of the titanium horn 114 propagates the vibrations directly to the blade 26 with minimal losses. The washers are thus aligned and compressed between the heel slug 118 and the horn 114. The compression of the piezo-ceramic washers 164 results in standing pressure waves propagated down the horn 114.

As stated previously, the piezo-ceramic washers 164 preferably occupy a node of vibration and other nodes appear exactly one half wavelength later and every half wavelength subsequently. Anti-nodes are located between the nodes and experience the largest longitudinal movement and the least stress. At 60 kilohertz, each ½ wavelength equals approximately 1.6 inches in the preferred titanium horn 114. The horn 114 is machined so that the transition region 136 desirably occupies a node. In addition, the coupling region 140 at the front portion of the horn 114 is preferably placed close to an anti-node to reduce the stress of the coupling. Thus, locations of the transition region 136 and the front coupling region 140 are multiples or fractions of the preferred ½ wavelength of 1.6 inches.

The heel slug 118 is preferably fabricated from tool steel or stainless steel. A central bore 178 extends through the heel slug 118 and includes internal threads 120 at the rear (proximal) end. The heel slug 118 also comprises two opposing wrench flats 180 at the rear end.

The parameters of the blade 26 may be altered, or the ultrasonic signal may be varied, to customize the type and character of incision desired. As stated previously, higher frequency surgical knives tend to propagate energy shorter distances into surrounding tissue and thus inflict less thermal damage. At times though, some thermal effect on the tissue is desirable, especially when dry cutting. Modulating a high frequency signal with a substantially lower carrier frequency allows the surgeon to nominally retain the advantageous features provided at high frequencies (hemostatis) while periodically applying a lower frequency to effectuate some increased degree of cavitation. At lower frequencies there is more drag, and thus more feel and tissue differentiation. Adjusting the modulating frequency to decrease the periods of high frequency results in more feel, and thus the surgeon may selectably alter the response of the surgical blade 26 to different types of tissue. In a preferred embodiment, the surgical blade 26 of the present invention is vibrated at 60 kHz with a modulating frequency of between 10 and 10,000 Hz, and a preferred frequency of 600 Hz.

Figure 18:
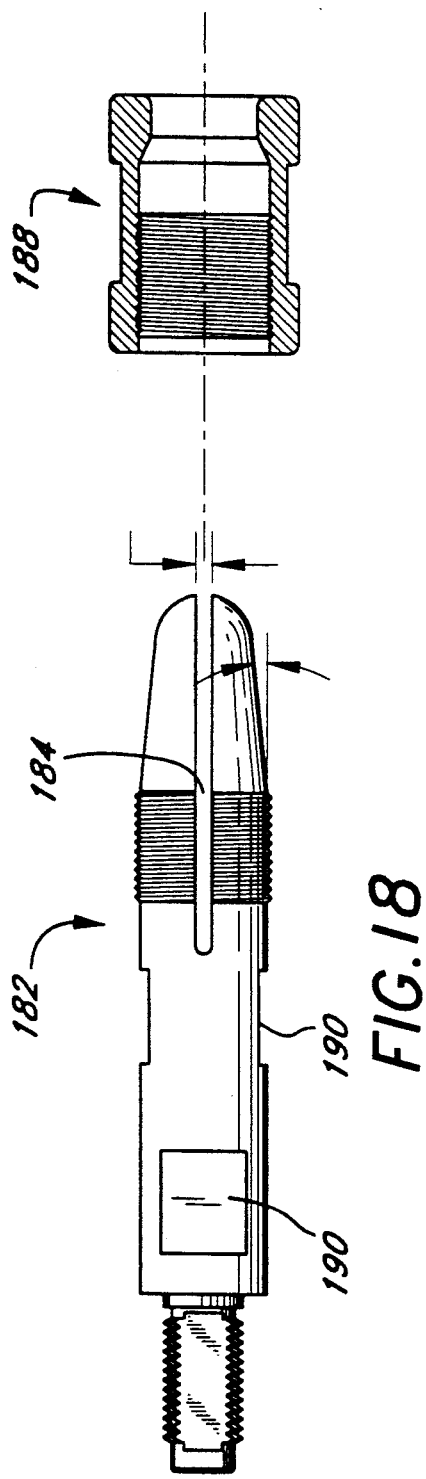
FIG. 18 is a side view of the split chuck and collet of FIG. 17 along lines 18—18.
Figure 17:
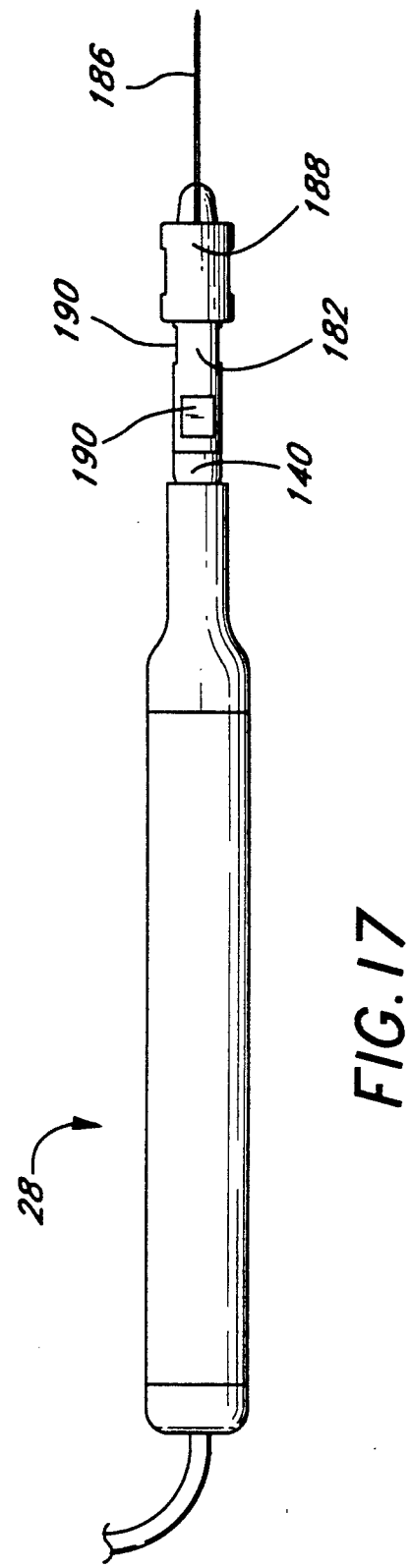
FIG. 17 is a top view of an ultrasonic medical tool of the present invention showing a handpiece, an extender and an alternative flat blade held in a split chuck.

Referring now to FIGS. 17 and 18, a split chuck 182 connects with an extender which couples with the handpiece 28 in an alternate form of the present invention. The split chuck 182 is shown in greater detail in FIG. 18. The split chuck 182 includes a forward slot 184 which receives a flat surgical cutting blade 186. The blade 186 is placed within the slot 184 and a collet 188 threads over the chuck 182 to tighten the blade within the chuck. Chuck 182 is provided with opposing wrench flats 190 to tighten the chuck in the handpiece 28, or an extender, with a wrench.

Advantageously, the extenders allow the handpiece of the present invention to be remain external to the body while the blade extends within a catheter for endoscopically-assisted surgery. The extenders possess excellent sonic transmission properties with minimal losses at the interfaces. Additionally, the rapid connect-/disconnect coupling feature allows rapid changing of extenders, blades and chucks. Preferably, the present invention may be used endoscopically with a 4 millimeter catheter opening. Preferably, extenders allow surgery at a depth of as much as 24 inches from the handpiece 28.

Figures 19, 20:
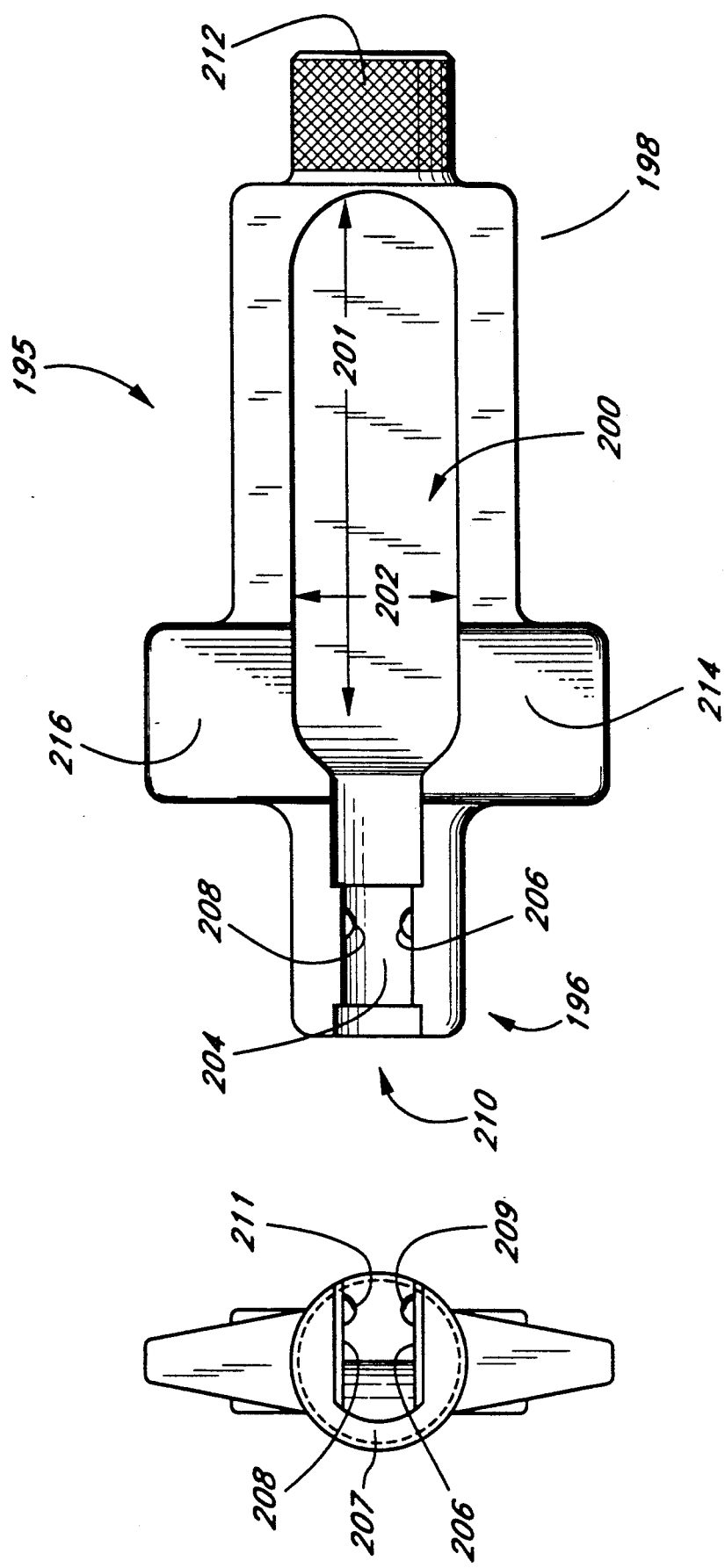
FIG. 19 illustrates a knife blade carrier in accordance with the present invention.
FIG. 20 is an end elevational view of the blade carrier of FIG. 19.

Referring to FIG. 19, there is disclosed a blade carrier 195 in accordance with a further aspect of the present invention. Blade carrier 195 facilitates handling of the ultrasonic surgical blade in a sterile environment prior to installation on an ultrasonic handpiece. In addition, the use of the blade carrier 195 minimizes the risk of inadvertent blade sticks during handling and installation of the blade.

Blade carrier 195 generally comprises a blade housing having a blade connector end 196, and a blade tip end 198. The overall length of the blade carrier 195 is preferably about 2.5 inches. Blade cavity 200 is disposed therebetween, for receiving the sharp end of the blade. The connection end of the blade, which may be threaded or provided with other quick connection/disconnection means previously disclosed, projects from the blade cavity 200 axially through the open channel 204 and out the open end 210. The open channel 204 is provided with a pair of opposing surfaces 206 and 208 for frictionally engaging the wrench flats on the connector end of a blade, as has been previously described. Referring to FIG. 20, opposing surfaces 206 and 208 can be more clearly seen. In a preferred embodiment, projections 209 and 211 are additionally provided for retaining the connection end of the blade within the open channel 204.

The blade cavity 200 is a shallow flat or rounded bottomed recess, having a length dimension 201 of about 1.5 inches and a width dimension 202 of about 0.50 sufficient to accommodate a variety of blade sizes. In general, blades contemplated to be utilized with the ultrasonic knife in accordance with the present invention have a cutting edge length within the range of from about 0.5 inches to about 1.5 inches. In addition, the width along the plane of the blade varies within the range of from about 0.030 inches to about 0.40 inches for most applications. Specialty blades, for unique applications, may vary considerably from the foregoing ranges.

The blade carrier 195 is provided at its blade tip end 198 with a knob 212. Knob 212 comprises a generally cylindrical body, preferably having a diameter of about 0.05 inches, and length of about 0.5 inches, having friction enhancing structures such as knurling on the radially exterior wall thereof. The axis of knob 212 is aligned with the axis extending through the open channel 204. In this manner, the clinician can spin the knob 212 between two fingers to threadably engage the connector on the knife with the corresponding connector on the ultrasonic handpiece or extender as discussed below.

The blade carrier 195 is preferably also provided with a pair of opposing wings 214 and 216 to provide leverage for rotating the blade carrier to tighten the connection between the blade and the ultrasonic knife handpiece. Preferably, the overall width of the carrier through the wings 214, 216 is about 1.2 inches. As has been previously discussed, the typical connection between the knife tip and the handpiece is a rotatably engagable connection. For example, with the quick connect and disconnect embodiment previously disclosed, the blade is inserted onto the handpiece or the connector by an axial advancement and then the blade is tightened by rotating the blade through an angle of approximately 90°. In an alternate embodiment, the blade is simply threaded onto the handpiece or connector by rotating through a series of complete revolutions. In either embodiment, the blade must be appropriately rotationally tightened into the handpiece or extender.

For this purpose, the opposing surfaces 206 and 208 and a hinge region 207 therebetween are preferably molded from a material having a suitable resilience that the rotation of the blade carrier 195 will rotate the blade contained therein until the blade is suitably tightened against the handpiece or extender. Further rotation of the blade carrier 195 will cause the opposing surfaces 206 and 208 to spread slightly, permitting relative rotation between the blade carrier 195 and the blade contained therein. The clinician simply rotates the blade carrier 195 until the assembly "snaps" or starts to cam over. In this manner, a predetermined predictable and repeatable amount of torque within the range of from about 0.50 to from about 0.80 inch-lbs., preferably about 3.0 inch-lbs., can be applied during installation of the blade. Wings 214 and 216 provide both a friction surface and leverage for the clinician to use to rotate the blade carrier 195 during installation. Following sufficient tightening of the blade, the blade carrier 195 is simply pulled laterally away from the tip of the blade and discarded, or saved, to be reinstalled at the end of surgery and then discarded with "sharps".

The blade carrier 195 may be constructed in any of a variety of ways which will be well known to one of skill in the art. For example, the entire blade carrier may be integrally molded such as by injection molding, thermo forming or vacuum forming of a pre-formed sheet of plastic. Alternatively, the blade carrier 195 can be fabricated from premolded component parts, such as by premolding the blade connection end 196 and the knob 212. The main body of the blade carrier 195 is preferably stamped or molded from a sheet of plastic, and may be thereafter secured to the blade connector end 196 and knob 212 using thermal bonding, solvent bonding, ultrasonic welding or other techniques known in the art.

Alternatively, some or all of the blade carrier 195 can be formed from an appropriate metal sheet, and preferably thereafter provided with an appropriate plastic coating. In general, the construction of the blade carrier 195 is of appropriate materials that will permit sterilization of the assembly of the blade carrier 195 with a blade therein. The blade carrier 195 and blade are thereafter introduced into a sealed packet or pouch for sterilization and shipment.

Problems associated with ultrasonic surgery can be generally classed in two categories. The first category would be the effect on the living tissue on either side of the cut. Excess heat generation, tearing of tissue or inadvertent cutting of nearby anatomical structures are all problematic to ultrasonic surgery. The second category of problems is a relative lack of operator comfort, flexibility and feedback.

In ultrasonic surgery, the knife blade may oscillate at any where within the range of from about 1 kHz to about 100 kHz. Typically, however, frequencies of lower than about 23 kHz are not used because they are within the audio range. In addition, frequencies in excess of about 50 or 60 Khz produce an excess amount of localized heating along the tissue contacting sides of the blades.

For relatively low frequencies, e.g. below about 20 or 30 kHz, high carbon steel or stainless steel is an appropriate construction material for the ultrasonic knife blades of the present invention. However, frequencies in excess of about 30 kHz, which are considered relatively high, are preferably used in conjunction with ultrasonic knife blades made from or coated with titanium, aluminum, or other metals or alloys which will transmit ultrasonic energy efficiently, with less internal heating.

Approximately 50% of the heat is produced from sound absorption in the surrounding tissue, 25% produced from internal frictional heating of the blade itself, and 25% produced by friction of the blade and tissue. At times, heat is preferred if a hemostatic nature of cut is desired. Hemostasis is the coagulation or formation of white gelatinous substance at the sides of the cut, and is commonly referred to as "bloodless surgery." At temperatures above 65° C. (149° F.), proteins in human tissue are denatured, producing coagulation. Although in some instances hemostasis is desirable, the increased temperatures involved in ultrasonic surgery potentially increase the likelihood of denaturing protein in tissue and can produce localized thermal damage, or necrosis, to the tissue surrounding the incision.

As mentioned above, sound absorption into the surrounding tissue comprises the majority of heat generation in ultrasonic surgery. Ultrasonic surgical instruments propagate pressure waves down the blade and into the surrounding tissue. At the interface of the blade material and the tissue, there is an impedance mismatch, causing the sound waves to dampen or "deaden" as they attempt to propagate further into the tissue. The energy absorbed by the damping characteristics of the tissue is converted to heat. Preferably, the ultrasonic energy does not propagate far into the tissue, to limit the negative effect the heat produces. It is well known that higher frequency, shorter wavelength signals dissipate faster and in shorter distances in elastic material, such as biological tissue, and therefore would appear to be favorable.

A smaller percentage of the total heat produced in an ultrasonic surgical procedure occurs from internal frictional heating of the knife blade. In general, the construction material of the surgical blade determines the level of internal friction, and potentially damaging heat. Stainless steel, for example, is a relatively inefficient conductor of acoustic energy, and a lot of internal friction results. Stainless steel, in fact, should not be used at frequencies above about 20 kHz as it gets too hot. The titanium used for the present surgical blade 26 on the other hand is an excellent conductor of acoustic energy and may be used at the highest frequency contemplated (60 kHz) with a minimum heat buildup, especially if caused to start and stop vibrating intermittantly. However, as stated previously, some heating may be necessary if bloodless surgery is desired.

Sharp surgical blades oscillating at ultrasonic frequencies can tend to fall through living tissue, much like a hot knife through butter. Conversely, a duller knife, or one which has low or no ultrasonic assistance, requires a greater amount of force, and more subsequent tearing of the tissue occurs. Such slower cutting, which may result in more scarring, may be desirable when performing surgery proximate vital organs so that the surgeon can feel the blade advancing through the tissue and more carefully continue. Ultimately, ultrasonic surgery results in the breaking of living tissue bonds which are of varying strengths. The present invention addresses this issue and provides the surgeon with multitudes of configurations of blades, depending on the type of cut desired.

The second category of problems associated with ultrasonic surgical tools are those relating to the lack of operator control of, and poor ergonomics of, the instruments. First, there has been a lack of understanding of the tactile feedback necessary to carefully resect different types of living tissues with one particular knife. As discussed above, a very sharp knife might be desirable, for instance in cosmetic surgery, but provide the surgeon with little or no feedback of the type of tissue the knife is cutting through. Conversely, a knife with lots of drag may provide feedback, but may have a substantial reduction in the quality of cut desired. Additionally, the amount of feedback desired is a subjective determination by the individual surgeon. A more experienced surgeon would tend to require less feedback than a novice. The amount of heat generated is another critical control parameter, previously addressed by simply altering the thermal footprint of the blade. Another phenomenon associated with ultrasonic surgery is the formation of cavitation bubbles in the region proximate the surgical blade. Control of the amount of cutting from mechanical shearing of the tissue bonds, as opposed to that from cavitation-assisted cutting, has not previously been addressed.

Cavitation occurs when the local pressure in a fluid decreases below the vapor pressure of that fluid. Local voids or vacuum pockets, in effect, are created which then tend to implode violently upon an increase in pressure. Objects moving rapidly through a fluid can induce such cavitation in their wakes by skin and form frictional forces, as is known in the art of fluid dynamics. Ultrasonically oscillating surgical blades have a tendency to cavitate in the bodily fluids surrounding an incision. In addition, normal saline or other fluids can be supplied to a surgical site to enhance normal cavitation. At lower frequencies, e.g., below about 20 to 30 kHz, ultrasonic knives tend to create a cavitation emulsification layer which nominally provides better lubrication for the knife blade, and tends to minimize the damage resulting from heat transfer to the surrounding tissue.

The amount of cavitation plays a major role in the characteristics of the final cut. The implosion of cavitation "bubbles" can be severely detrimental to the surgical instrument, but also can assist the cutting action by breaking tissue bonds at the same time. The physics of the formation of cavitation bubbles is such that the temperature at their surface can reach 5000° F. This intense but highly localized energy is converted to the kinetic energy of a shock wave upon implosion. The result is that the knife tends to "blow through" the tissue and the energy which would have been converted to thermal transfer to the surrounding tissue is used for cutting. In some instances cavitation primarily, in conjunction with some hemostatic action, is a preferred cutting method.

The present invention addresses the aforementioned problems associated with ultrasonic surgery in terms of varying the characteristics of the incision and providing the surgeon with proper feedback and flexibility of use. The surgeon has a wide range of blade configurations and operating modes to best perform a particular procedure to his or her preference. The tactile feedback and cutting options available with the present ultrasonic surgical blade are a major improvement over prior instruments.

The amount of heat generated and propagated into the surrounding tissue is controlled by the shape of the preferred blade 26. The area of the contact surfaces 38 can be widened to increase the heat generation from sonic and conductive energy transfer. This is desirable in regions containing numerous blood vessels to induce hemostasis. Similarly, the angle of the tapers 40,42 affects the magnitude of thermal footprint of the blade 26. A large portion of the cross-section of the blade 26 in contact with the tissue being cut is removed by the formation of the relief 36. These parameters can be cohesively managed to provide a wide range of incision characteristics. For example, cosmetic surgery requires the sharpest blade with minimal thermal damage to minimize scarring. Alternatively, a sharp blade with more heat generation may require a similar blade tip with more contact surface and less relief in the central portion. The various shapes of the current blade 26 contemplate an infinite number of functional combinations.

Another factor in heat generation is the surface texture of the blade 26 surfaces. Smoother surfaces result in less frictional resistance than rougher ones. Roughening the surface texture of the contact surfaces 38, while highly polishing the tapers 40, 42 and relief portions 36, results in some increase in heat generation, which can be customized for the type of tissue involved. Surface textures can be modified by either polishing an existing surface or roughening the existing surface of the blade. Minimal surface friction will be incurred in a blade having a highly polished surface such as an RMS of 1 or 2. RMS, or root-mean-square, is a proportionate term generally referring to the statistical average of the sizes of irregularities. Practically, however, polishes of this degree are difficult to produce on the construction material utilized for surgical blades. Relatively rough areas of the surgical blades disclosed herein are contemplated to have an RMS of about 63. This level of roughening can be accomplished by processing the knife blade with glass beading, chemical etching, or other techniques which will be known to one of skill in the art. Preferably, a random sized distribution of bumps or pockets within the range of from about 20 to about 100 micron are utilized. The bumps or pockets are preferably rounded or hemispherical in shape, to improve longevity under ultrasonic vibration conditions, and to minimize fragmentation and leaving parent material behind.

A further parameter influencing the amount of thermal generation is the frequency and mode of oscillations. The control system 30 of the present invention allows for complete flexibility for the surgeon to alter the oscillation character. As is known, a higher frequency surgical blade tends to transfer less thermal energy at a greater depth via sound propagation to the surrounding tissue but has higher internal heat of blade and at the interface of blade and tissue. The control system 30 provides a means for modulating such an advantageous frequency with lower frequencies to provide some drag, or tactile feedback, to the surgeon, and increase effective cavitation. Other combinations of frequencies and wave forms can be generated by the control system 30 to tailor the oscillations of the blade 26 to the particular surgical environment.

The present invention also identifies and presents solutions to the problems of feedback and individual surgeon needs. The advantageous shape of the serrations of the present blade 26 transfer resistance forces more efficiently to the hand of the surgeon. Providing surfaces perpendicularly vectored to the tissue means that more resistance is encountered from an increase in the pressure of cut. Reducing the stroke of the blade and spacing the teeth 46 of the blade 26 so that at least two teeth 46 encounter a specific tissue bond on each stroke reduces the internal stresses on the knife as well as the magnitude of vibrations of the handpiece, while ensuring a clean and effective cut.

Another benefit of the ultrasonic surgical system 24 of the present invention is the ability to manage the amount of cavitation generated. Cavitation minimizes thermal energy penetration into the surrounding tissue by converting the transient shock wave energy into a cutting action. The dynamic feedback associated with cavitation-assisted cutting provides enhanced tissue differentiation, as the stronger, more elastic, bonds holding such anatomical structures as blood vessels together require more energy to break than does the surrounding tissue. The feedback from cavitation cutting, in effect, increases the change in drag felt when cutting from weak to tough tissue, as opposed to the minimal change in feedback from simply mechanically shearing the same tissue layers.

Control of the various parameters of the present invention allows the surgeon to select the amount of cavitation produced. The primary factor for changing the amount of cavitation at a fixed frequency and a uniform saline solution is the surface texture of the blade 26 surfaces. Smoother surfaces result in less frictional resistance than rougher ones and thus less disturbance of the fluid boundary layer next to the blade. Roughening the surface texture of a blade results in wakes and the subsequent formation of cavitation bubbles. In general, the larger the surface irregularity, the larger and more energetic bubble that is formed. The discussion of surface roughness of the blade 26 above in terms of preferred frictional heating applies to cavitation as well. Relatively rough areas of the surgical blades disclosed herein to induce a substantial amount of cavitation are contemplated to have an RMS of about 63.

Cavitation can also be increased by increasing the angle and width of the blade cross-section which contacts the tissue. The shape and surface texture of the teeth of the present blade can be altered to increase or decrease cavitation or, in effect, manage the percentage of cutting due to cavitation.

Cavitation is highly dependent on the frequency of oscillation. Lower frequencies, in general, produce more cavitation as slower moving blades tend to form larger bubbles; there is approximately nine time more cavitation energy at 20 kHz than at 60 kHz for the same stroke (peak to peak motion). The present invention advantageously can be configured to increase the amount of cavitation at higher frequencies. In addition to altering the shape and texture of the blade, the blade 26 oscillation may be started and stopped with gated pulses to induce more cavitation. A blade operating at 60 kHz to take advantage of the reduced thermal penetration, for example, may be gated to cause a greater number of larger cavitation bubbles to form during the slow-down and start-up periods without increasing the thermal effect on the surrounding tissue. The depth of thermal penetration is desirably limited to 1 mm into the sides and bottom of an incision. Advantageously, the gated pulses would be applied directly out of phase from the original frequency to rapidly dampen out the natural vibration of the oscillating blade 26 and horn 114. The gated pulse would preferably only reduce the vibrational amplitude to 5-10% of the original and thus leave the blade and horn "singing". The start up pulse would then be applied directly in synchronous phase with the small residual vibrations, to more quickly bring the blade 26 and horn 114 back to the original amplitude.

Another primary advantage with the surgical knife of the present invention is seen in its ability to cut through a wide range of materials with a maximum of control. Coordinating the blade 26 configuration, ultrasonic signal shape and surgical technique permit an infinite number of applications. For example, in the area of tissue resection, straight cutting or dry cutting with hemostasis, or cavitation-assisted cold-cutting are all within the realm of uses for the present invention. Similarly, other more durable materials may be cut with the present blade 26. Osseous matter can be sawed easily and with minimal necrosis. Plastics and cements, such as PMMA used in affixing prosthetic devices within body cavities, are also rapidly cut through with the proper toothed blade 26 and at the proper frequency. Another possible use for the present invention is for delaminating hi-tech composites, the vibrations serving to break the chemical bonds of the laminates.

A further configuration possible with the blade 26 of the present invention is machining more than one shaped edge around the blade. This time-saving feature would provide a surgeon with essentially two or more tools in one. Normally, a surgical incision passes through many different types of tissue, requiring different techniques or a new blade altogether. The time spent switching a blade can be extremely costly to the patient. The present surgical blade 26 may have one side shaped and finished for rapid, sharp cutting through outer layers of tissue. The other edge of the blade may have a rougher wider shape to induce more cavitation and drag, for "teasing" the blade through tissue close to vital organs. Other possibilities include edges preferred for cold-cutting (more cavitation), cauterizing (localized heating) or bone cutting (minimum heating).

Finally, the variations of blade and oscillation character provide the knowledgeable surgeon with a highly advanced and flexible surgical tool. The numerous combinations of the aforementioned surgical knife parameters give the surgeon ultimate freedom in choosing the preferred embodiment.

The present invention has been described in terms of certain preferred embodiments. However, additional embodiments and variations will become apparent to one of skill in the art in view of the disclosure contained herein. Such variations are intended to be within the scope of the present invention. Accordingly, the scope of the present invention is not limited by the specific embodiments disclosed herein, but is to be defined by reference to the appended claims.

We claim:

1. An ultrasonic knife, comprising:
    a source of ultrasonic vibrations;
    a knife blade coupled to the source; and
    a control for selectively causing the source to produce ultrasonic vibrations, thereby inducing reciprocal movement of the knife blade through a predetermined stroke length;
    said blade comprising at least two teeth defining a recess therebetween, wherein the distance between the two teeth is no more than about the predetermined stroke length.

2. An ultrasonic knife as in claim 1, wherein the distance between the two teeth, is no more than about 80% of the predetermined stroke length.

3. An ultrasonic knife as in claim 1, wherein the predetermined stroke length is within the range of from about 0.001 to about 0.002 inches.

4. An ultrasonic knife as in claim 3, wherein the predetermined stroke length is approximately 0.0015 inches.

5. An ultrasonic knife as in claim 1, wherein the width of each of the two teeth is within the range of from about 30% to about 60% of the stroke length.

6. An ultrasonic knife as in claim 5, wherein said width is about 50% of the stroke length.

7. An ultrasonic knife as in claim 1, wherein the recess comprises a bottom portion and two side wall portions, each sidewall portion terminating in a tooth edge, and a distance between the bottom and the tooth edge within the range of from about 20% to 100% of the stroke length.

8. An ultrasonic knife as in claim 7, wherein the distance between the bottom and the tooth edge is approximately 80% of the stroke length.

9. An ultrasonic knife as in claim 7, wherein the bottom and the sidewalls of the recess are generally parabolic in shape.

10. An ultrasonic knife as in claim 7, wherein the two sidewalls are generally parallel to each, and generally perpendicular to the bottom of the recess.

11. An ultrasonic knife as in claim 7, wherein the two sidewalls and the bottom of the recess define a continuous boundary of the recess, and at least portion of the boundary extends at a perpendicular to the longitudinal axis of ultrasonic energy propagation of the knife, and at least a second portion extends generally parallel to the longitudinal axis of ultrasonic energy through the knife.

12. An ultrasonic knife as in claim 1, wherein said blade comprises a generally planar body portion having a proximal connection end and at least one cutting edge thereon, said blade having a width in the central region thereof which is less than the width at least one point between the central region thereof and the cutting edge.

13. An ultrasonic knife as in claim 1, further comprising an ultrasonic extender for extending the distance between said source and the blade.

14. An ultrasonic knife as in claim 1, wherein said knife blade comprises a generally planar body having at least one cutting edge thereon.

15. An ultrasonic knife as in claim 14, wherein said planar body has a generally parabolic shape defined by a pair of generally opposing cutting edges and an arcuate distal cutting edge.

16. An ultrasonic knife as in claim 14, wherein said planar body comprises a pair of generally opposing flat tissue contact surfaces positioned proximate to said cutting edge.

17. An ultrasonic knife as in claim 14, wherein said planar body comprises a shallow recess on the side of the planar body for reducing the thermal footprint of the blade.

18. An ultrasonic knife as in claim 14, wherein the planar body comprises a roughened surface region thereon.

19. An ultrasonic knife as in claim 18, wherein said roughened surface region has a root-means-square surface roughness of about 20 or greater.

20. A method of cavitation assisted surgery utilizing a surgical knife, comprising:
providing an ultrasonic knife of the type having a source of ultrasonic vibrations, a knife blade coupled to the source, said knife blade having a surface texture comprising a plurality of rounded spherical or hemispherical irregularities, having a width of within the area of about 20 to about 100 microns, and a control for selectively causing the source to produce ultrasonic vibrations in the knife blade;
activating the source to induct reciprocal movement of the knife blade throughout a predetermined axial stroke amplitude;
contacting the blade with a tissue to be cut;
inducing the formation of cavitation bubbles in the fluid media surrounding the knife blade; and
permitting the cavitation bubbles to implode, thereby producing shockwaves for breaking the tissue bond adjacent a cutting edge of the knife blade.

21. A method as in claim 20, wherein said inducing formation of cavitation bubbles is assisted by providing a plurality of surfaces on the cutting edge of the knife which extend generally perpendicular to the longitudinal axis of ultrasonic energy propagation through the knife.

22. A method as in claim 20, wherein said inducing formation of cavitation bubbles step comprises modulating the energy driving the knife to include at least a first low frequency component for increasing cavitation, and a high frequency component for minimizing the depth of penetration of heat from the blade into the tissue.

* * * * *